United States Patent [19]
Aberg et al.

[11] Patent Number: 5,807,541
[45] Date of Patent: *Sep. 15, 1998

[54] NSAID/FLUORIDE PERIODONTAL COMPOSITIONS AND METHODS

[75] Inventors: Gunnar Aberg, Westborough; Thomas Patrick Jerussi, Framingham; John R. McCullough, Worcester, all of Mass.

[73] Assignee: Sepracor, Inc., Marlborough, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 636,150

[22] Filed: Apr. 22, 1996

[51] Int. Cl.$^6$ .............................. A61K 7/16; A61K 7/18; A61K 33/16
[52] U.S. Cl. ............................ 424/52; 424/673; 424/676
[58] Field of Search ............................................. 424/49–58

[56] References Cited

U.S. PATENT DOCUMENTS

| | | | |
|---|---|---|---|
| 4,933,172 | 6/1990 | Clark, Jr. et al. | 424/49 |
| 5,190,981 | 3/1993 | Wechter | 514/900 |
| 5,240,696 | 8/1993 | Van Der Ouderaa et al. | 424/49 |
| 5,294,433 | 3/1994 | Singer et al. | 424/52 |
| 5,364,616 | 11/1994 | Singer et al. | 424/52 |
| 5,464,609 | 11/1995 | Kelm et al. | 424/54 |
| 5,500,206 | 3/1996 | Charbonneau | 424/50 |
| 5,500,448 | 3/1996 | Cummins et al. | 514/717 |

FOREIGN PATENT DOCUMENTS 6-305946 of 1994 Japan.

OTHER PUBLICATIONS

Offenbacher et al. "Effects of NSAIDs on beagle crevicular cyclooxygenase metabolites . . . " *J. Periodontal Res.*27, 207–213 (1992).

Jeremy et al. "Differential inhibitory potencies of non–steroidal antiinflammatory . . . "*E. J. Pharm. 182*, 83–89 (1990).

Dodam et al. "Effect of fluoride on cardiopulmonary function and release of . . . " *J. Appl. Physiol.*, 569–577 (1995).

Kawase et al. "Aluminofluoride—and Epidermal Growth Factor–Stimulated DNA Synthesis" *Pharmacol. Toxicol.* 69 330–337 (1991).

Kopczyk et al. "Clinical and Microbiological Effects of a Sanguinaria–Containing Mouthrinse . . . " *J. Periodontol.* 62, 617–622 (1991).

Honda et al. "Introduction of Cyclo–oxygenase Synthesis in Human . . . " *Biochem. J.*272, 259–262 (1990).

Parker et al. "Prevalence and severity of periodontitis in a high fluoride area" *Comm. Dental Oral Epido* 13 108–112 (1985).

*Primary Examiner*—Shep K. Rose
*Attorney, Agent, or Firm*—Heslin & Rothenberg, P.C.

[57] ABSTRACT

A method for preventing dental caries by administering fluoride and, at the same time controlling periodontal bone loss precipitated by the fluoride, by providing a combination of fluoride and NSAID is disclosed. Topical medicament compositions including NSAIDS and fluoride are also disclosed.

2 Claims, 1 Drawing Sheet

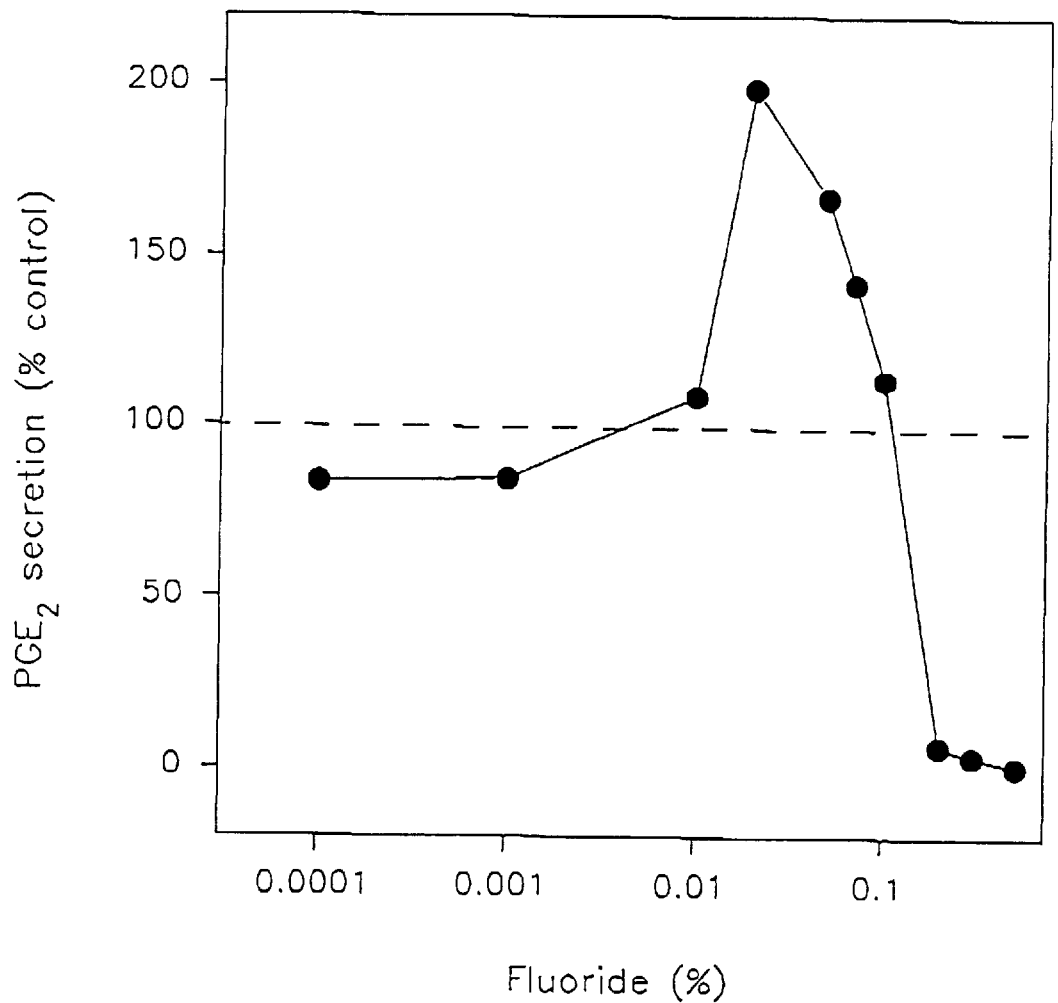

NSAID/FLUORIDE PERIODONTAL COMPOSITIONS AND METHODS

FIELD OF THE INVENTION

The invention relates to dental compositions. In another aspect this invention relates to methods and compositions for controlling periodontal bone loss.

BACKGROUND OF THE INVENTION

The role of topical and systemic fluoride in the inhibition of dental caries is well established. There is good evidence that professionally applied topical fluoride and the use of dentifrices and mouthwashes containing fluoride are effective in preventing dental caries among high risk patients. The amount of fluoride ion employed in most dentifrices and mouthwashes ranges from 0.05 to 0.15% weight-to-volume. Most commonly sodium fluoride, and sodium monofluorophosphate, less commonly, stannous fluoride and amine fluoride, are employed as sources of fluoride ion.

It is also known that under certain circumstances sodium fluoride and fluoroaluminates can activate G proteins and thereby induce prostaglandin production in endothelial cells and leukotriene production in platelets, granulocytes and monocytes. The metabolites of arachidonic acid have been implicated as important biochemical mediators of tissue destruction in various inflammatory diseases.

The term periodontal diseases relates to conditions in which the gingiva and underlying alveolar bone are attacked. The condition exists in a number of species of warm blooded animals including humans and canines, and appears at least initially to involve an inflammatory and immunological response to the stimulus of bacterial plaque. Clinically, the advance of the disease involves conversion of chronic gingivitis, involving primarily inflammation of the gingiva, to chronic destructive periodontitis, in which resorption of the alveolar bone, increased mobility of the teeth, and in advanced stages, loss of teeth are observed.

SUMMARY OF THE INVENTION

We have found that fluoride, in the concentration range in which it is employed for the prevention of dental caries, stimulates the production of prostaglandins and thereby exacerbates the inflammatory response in gingivitis and periodontitis.

The present invention is a method for preventing dental caries by administering a fluoride salt into the oral cavity while at the same time controlling periodontal bone loss by administering, in addition to the fluoride salt, an amount of an NSAID sufficient to inhibit the production of prostaglandins induced by the fluoride.

In one aspect the invention relates to a method for preventing dental caries and at the same time controlling periodontal bone loss which comprises administering into the oral cavity a fluoride salt together with a therapeutically effective amount of an NSAID, particularly a propionic acid or acetic acid NSAID. More particularly, the method comprises administering (a) an amount of a fluoride salt sufficient to stimulate eicosanoid anabolism and (b) an amount of an NSAID sufficient to counteract the stimulation of eicosanoid anabolism that arises from the administration of the fluoride ion. Preferred NSAIDS include racemic ketoprofen and its enantiomers, racemic ketorolac and its enantiomers and racemic flurbiprofen and its enantiomers. S-ketoprofen, S-flurbiprofen and R-ketorolac are particularly preferred. In the method of the invention, the fluoride salt and NSAID may be administered as a toothpaste or a mouth wash.

In another aspect the invention relates to a composition comprising (a) a fluoride salt; (b) a therapeutically effective amount of a propionic or acetic acid NSAID; and (c) a pharmaceutically acceptable carrier for topical application in an oral cavity. Preferred compositions are dentifrices and mouth washes containing an amount of fluoride salt sufficient to stimulate eicosanoid anabolism; an amount of NSAID sufficient to counteract the stimulation of eicosanoid anabolism; and a pharmaceutically acceptable carrier. Preferred sources of fluoride ion are sodium fluoride, sodium monofluorophosphate and stannous fluoride, providing fluoride at from 0.01 to 0.2%, preferably 0.01 to 0.1%, weight-to-volume at the alveolar surface. The appropriate NSAID may be present at from $2.5 \times 10^{-3}$ to 5% by weight.

BRIEF DESCRIPTION OF THE DRAWING

FIG. 1 is a graph of percent increase in prostaglandin $E_2$ output as a function of fluoride ion concentration in human promyelocytic leukemia cells.

DETAILED DESCRIPTION

The present invention is based on the discovery that fluoride ion at concentrations between about 5 and about 50 mM stimulates the production of prostaglandin $E_2$, ($PGE_2$) reaching a peak of 200% of control at about 10 mM. Increased synthesis of cyclooxygenase products, especially $PGE_2$ and thromboxane $A_2$ have been associated with an increased severity and progression of periodontal lesions in humans. Offenbacher et al. [*J. Periodontal Research* 27, 207–213 (1992)] have presented data that support the concept that the increase in $PGE_2$ and thromboxane which occurs during disease progression is not a result of an epiphenomenal association with tissue destruction, but rather represents a cell mediated process which directly elicits tissue damage. Thus, the inclusion of fluoride in toothpastes and mouthwashes for the purpose of inhibiting the development of caries may, at the same time, accelerate the process of chronic, destructive periodontitis. According to the present invention, an NSAID, which inhibits products of the cyclooxygenase pathway, is combined with fluoride to provide a medicament that inhibits the development of both dental caries and periodontal bone loss. The fluoride ion is present at a concentration which is effective to prevent caries but, which in the absence of a cyclooxygenase inhibitor, would promote periodontal bone loss. The NSAID is present at a concentration that effectively inhibits the fluoride-stimulated production of prostaglandins.

We have found that the dose response curve for fluoride ion-induced stimulation of prostaglandins is biphasic. At concentrations below about 5 mM (i.e., below about 0.01% w/v), fluoride has no significant effect on stimulated $PGE_2$ secretion; above about 50 mM (i.e., above about 0.1% W/v), fluoride ion becomes inhibitory to $PGE_2$ secretion. The concentration of sodium fluoride found in currently marketed dentifrices (0.15%), when it is diluted with saliva, gives rise to solutions that are presumably below about 50 mM at the alveolar surface, and therefore stimulate prostaglandin production. It may be contemplated that a dentifrice or mouthwash that provided concentrations of fluoride greater than about 50 mM at the alveolar surface would inhibit both caries formation and periodontal bone loss. Unfortunately, fluoride ion is extremely toxic and the therapeutic ratio is quite small. As a result, if the dose of fluoride in the composition is increased to provide an oral concentration of fluoride ion that would fall in the inhibitory range of the $PGE_2$ secretion curve, safety becomes an issue. We have found that the addition of an NSAID to the fluoride-containing composition reduces the stimulatory effect of fluoride on prostaglandin levels, and enables one to take advantage of the caries-preventing activity of non-toxic doses of fluoride while not exacerbating periodontitis.

NSAIDS can be characterized into five groups:
(1) the propionic acids;
(2) the acetic acids;
(3) the fenamic acids;
(4) the biphenylcarboxylic acids; and
(5) the oxicams.

"Propionic acid NSAIDS" as defined herein are non-narcotic analgesics/nonsteroidal antiinflammatory drugs having a free —$CH(CH_3)COOH$ group, which optionally can be in the form of a pharmaceutically acceptable salt group, e.g., —$CH(CH_3)COO^-Na^+$. The propionic acid side chain is typically attached directly or via a carbonyl function to a ring system, preferably to an aromatic ring system. Exemplary propionic acid NSAIDS include: ibuprofen, indoprofen, ketoprofen, naproxen, benoxaprofen, flurbiprofen, fenoprofen, fenbufen, pirprofen, carpofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

As is evident from the structural formula above, profens exist in enantiomeric forms. NSAIDs from other classes may also exhibit optical isomerism. The invention contemplates the use of pure enantiomers and mixtures of enantiomers, including racemic mixtures, although the use of the substantially optically pure eutomer will generally be preferred. "Acetic acid NSAIDS" as defined herein are non-narcotic analgesics/nonsteroidal antiinflammatory drugs having a free —$CH_2COOH$ group (which optionally can be in the form of a pharmaceutically acceptable salt group, e.g. —$CH_2COO^-Na^+$, typically attached directly to a ring system, preferably to an aromatic or heteroaromatic ring system. Exemplary acetic acid NSAIDS include: ketorolac, indomethacin, sulindac, tolmetin, zomepirac, diclofenac, fenclofenac, alclofenac, ibufenac, isoxepac, furofenac, tiopinac, zidometacin, acematacin, fentiazac, clidanac, oxpinac, and fenclozic acid. Structurally related acetic acid derivatives having similar analgesic and antiinflammatory properties are also intended to be encompassed by this group.

"Fenamic acid NSAIDs" are non-narcotic analgesics/nonsteroidal antiinflammatory drugs having a substituted N-phenylanthranilic acid structure. Exemplary fenamic acid derivatives include mefenamic acid, meclofenamic acid, flufenamic acid, niflumic acid, and tolfenamic acid.

"Biphenylcarboxylic acid NSAIDS" are non-narcotic analgesics/nonsteroidal antiinflammatory drugs incorporating the basic structure of a biphenylcarboxylic acid. Exemplary biphenylcarboxylic acid NSAIDs include diflunisal and flufenisal.

"Oxicam NSAIDs" are N-aryl derivatives of 4-hydroxyl-1,2-benzothiazine 1,1-dioxide-3-carboxamide. Exemplary oxicam NSAIDs are piroxicam, sudoxicam and isoxicam.

The effects of fluoride ion, as sodium fluoride, were studied on $PGE_2$ secretion in human promyelocytic leukemia cells at 10 concentrations in duplicate (from 52 $\mu$m to 0.26M) to evaluate its inhibitory and stimulatory effects on a wide range of concentrations. The method is described in an article by Honda et al. [*Biochem. J.* 272, 259–262 (1990)], the entire disclosure of which is incorporated herein by reference. Results are expressed as a percentage of control after subtraction of background. The $IC_{50}$ value and Hill coefficient ($n_H$) were determined by non linear regression analysis of the competition curve. These parameters were obtained by Hill equation curve fitting using the Sigmaplot™ software (Jandel). The effects of fluoride tested at the ten concentrations are illustrated in FIG. 1, for which the numerical values are reported in Table I:

TABLE 1

| F % (molarity) | % Control | | |
|---|---|---|---|
| | 1st Value | 2nd value | mean |
| 0.0001 (52 $\mu$M) | 80.1 | 87.4 | 83.7 |
| 0.001 (520 $\mu$M) | 94.1 | 74.9 | 84.5 |
| 0.01 (5.2 mM) | 117.7 | 99.8 | 108.7 |
| 0.02 (10.4 mM) | 188.7 | 208.8 | 198.8 |
| 0.05 (26 mM) | 157.9 | 177.3 | 167.6 |
| 0.07 (36 mM) | 142.1 | 142.1 | 142.1 |
| 0.1 (52 mM) | 115.1 | 112.6 | 113.9 |
| 0.2 (104 mM) | 5.2 | 8.9 | 7.0 |
| 0.3 (156 mM) | 4.9 | 3.1 | 4.0 |
| 0.5 (260 mM) | 0.5 | 1.7 | 1.1 |

Racemic ketoprofen and its enantiomers were tested alone and in combination with fluoride for inhibition of prostaglandin production in HL-60 cells. Compounds were screened in duplicate at the following concentrations: $10^{-10}$, $10^{-9}$, $10^{-8}$ and $10^{-7}$M for ketoprofen, and 0.05, 0.1, and 0.5% for fluoride as NaF. The data are tabulated below. Numbers in Table II represent % inhibition of $PGE_2$; those in parentheses ( ) indicate % stimulation.

TABLE II

| Fluoride Concentration | Ketoprofen Concentration | | | |
|---|---|---|---|---|
| | $10^{-10}$ M | $10^{-9}$ M | $10^{-8}$ M | $10^{-7}$ M |
| none | — | 40 | 63 | 82 |
| 26 mM | (125) | (125) | — | 66 |
| 52 mM | — | 11 | 46 | 85 |
| 260 mM | 102 | 101 | 97 | 98 |

Fluoride alone at the 26 mM concentration (0.05%) caused a 108% stimulation of $PGE_2$ production, whereas inhibition of 12 and 92% were respectively observed at 52 mM and 260 mM (data not in Table II). In combination with low concentrations of ketoprofen, a stimulation (125%) was also observed. However at the highest concentration of ketoprofen ($10^{-7}$), the stimulation induced by $F^-$ was overcome. In fact, at 260 mM fluoride, $PGE_2$ production was totally inhibited by $10^{-10}$M ketoprofen, whereas inhibition by $10^{-10}$M of ketoprofen alone was undetected, and in another study, the same concentration of ketoprofen inhibited $PGE_2$ levels only 26%. The data from racemic ketoprofen alone (no F) and racemic ketoprofen plus 52 mM fluoride were then plotted, fit with regression lines, and $IC_{50}$s calculated: RS-ketoprofen $IC_{50}$=2.8 nM; RS-ketoprofen+52 mM F $IC_{50}$=11.8 nM. Fluoride at 0.1 % (52 mM) increased the $IC_{50}$ for ketoprofen alone by approximately 4-fold. However, the ketoprofen curve was not merely shifted to the right (indicative of competitive antagonism), but rather, as the concentration of ketoprofen was increased, the antagonistic effect of $F^-$ was diminished. Therefore it appeared that ketoprofen and $F^-$ were not competing at the same site.

The effects of (R)- and (S) ketoprofen associated with sodium fluoride on A23187-induced $PGE_2$ secretion are indicated in Tables III and IV. The results are expressed as % of control; they are the mean of two determinations. The $IC_{50}$ value determined for indomethacin under the same conditions (in the absence of fluoride) was $9.2 \times 10^{-10}$M.

TABLE III

Effects of (R)-Ketoprofen and Fluoride on A23187-Induced $PGE_2$ Secretion

| (R)-Ketoprofen (M) | F (%) | % Inhibition | % stimulation (stimulation factor) |
|---|---|---|---|
| 0 | 0.05 | | 16 (×1.16) |
| 0 | 0.1 | 26 | |
| 0 | 0.5 | 96 | |
| $10^{-10}$ | 0 | 14 | |
| $10^{-9}$ | 0 | 6 | |
| $10^{-8}$ | 0 | 39 | |
| $10^{-7}$ | 0 | 81 | |
| $10^{-10}$ | 0.05 | | 27 (×1.27) |
| $10^{-9}$ | 0.05 | | 14 (×1.14) |
| $10^{-8}$ | 0.05 | 5 | |
| $10^{-7}$ | 0.05 | 47 | |
| $10^{-10}$ | 0.1 | 23 | |
| $10^{-9}$ | 0.1 | 2 | |
| $10^{-8}$ | 0.1 | 32 | |
| $10^{-7}$ | 0.1 | 75 | |
| $10^{-10}$ | 0.5 | 98 | |
| $10^{-9}$ | 0.5 | 99 | |
| $10^{-8}$ | 0.5 | 99 | |
| $10^{-7}$ | 0.5 | 100 | |

TABLE IV

Effects of (S)-Ketoprofen and Fluoride on A23187-Induced $PGE_2$ Secretion

| (S)-Ketoprofen (M) | F (%) | % Inhibition | % stimulation (stimulation factor) |
|---|---|---|---|
| 0 | 0.05 | | 16 (×1.16) |
| 0 | 0.1 | 26 | |
| 0 | 0.5 | 96 | |
| $10^{-10}$ | 0 | 10 | |
| $10^{-9}$ | 0 | 70 | |
| $10^{-8}$ | 0 | 89 | |
| $10^{-7}$ | 0 | 96 | |
| $10^{-10}$ | 0.05 | | 27 (×1.22) |
| $10^{-9}$ | 0.05 | 35 | |
| $10^{-8}$ | 0.05 | 82 | |
| $10^{-7}$ | 0.05 | 95 | |
| $10^{-10}$ | 0.1 | 18 | |
| $10^{-9}$ | 0.1 | 54 | |
| $10^{-8}$ | 0.1 | 89 | |
| $10^{-7}$ | 0.1 | 98 | |
| $10^{-10}$ | 0.5 | 100 | |
| $10^{-9}$ | 0.5 | 100 | |
| $10^{-8}$ | 0.5 | 98 | |
| $10^{-7}$ | 0.5 | 99 | |

To summarize, fluoride has no effect on $PGE_2$ secretion from 0.0001 to 0.01%. It induces stimulation from 0.02 to 0.07% (maximum at 0.02% with a 99% stimulation) and then it completely inhibits $PGE_2$ secretion above 0.2%. S-Ketoprofen is more potent than R-ketoprofen; they respectively inhibit $PGE_2$ secretion with $IC_{50}$ values of around $4 \times 10^{-10}$ and $1 \times 10^{-7}$M.

In the presence of fluoride, the effects of R- and S-ketoprofen are modified. At 26 mM, fluoride induces a decrease of the inhibitory effects of R- and S-ketoprofen; in contrast at 260 mM, fluoride amplifies its inhibitory effects. These results are in accordance with the stimulatory and inhibitory effects observed with fluoride alone.

The preferred NSAIDs for use in mouthwashes and dentifrices are propionic and acetic acids and their pharmaceutically acceptable salts. Typical formulations are shown below:

| Ingredient | Parts |
|---|---|
| Toothpaste Composition | |
| Example 1A | |
| S(+) Flurbiprofen | 1.0 |
| Magnesium aluminum silicate | 1.0 |
| Dicalcium phosphate | 47.0 |
| Sodium carboxymethylcellulose | 0.5 |
| Mint flavor | 4.0 |
| Sodium lauryl sulfate | 2.0 |
| Benzoic acid | 0.1 |
| Sodium monofluorophosphate | 0.73 |
| Water | 44.4 |
| Example 1B | |
| Deionized Water | 28.0 |
| Glycerine | 25.0 |
| Silica | 40.0 |
| Sodium Lauryl Sulfate | 1.2 |
| Mint Flavor | 1.0 |
| Xanthan Gum | 1.0 |
| Sodium Benzoate | 0.5 |
| Sodium Saccharin | 0.3 |
| Sodium Fluoride | 0.24 |
| Titanium Dioxide | 0.5 |
| Ketoprofen | 2.5 |
| Mouthwash Composition | |
| Example 2 | |
| Alcohol U.S.P. | 15.0 |
| Sorbitol | 20.0 |
| Pluronic F-127 | 1.0 |
| Flavor | 0.4 |
| Sodium Saccharin | 0.03 |
| Sodium Fluoride | 0.05 |
| Ketorolac | 1.0 |
| Deionized Water q.s. | 100.00 |

We claim:

1. A method for preventing dental caries and at the same time controlling periodontal bone loss which comprises administering, together with an amount of a fluoride salt sufficient to provide a 0.01% to 0.1% solution of fluoride at an alveolar surface, an amount of S-ketoprofen sufficient to provide a $10^{-7}$ to $10^{-9}$M solution of S-ketoprofen at said alveolar surface.

2. A method according to claim 1 wherein said fluoride salt and said S-ketoprofen are administered as a toothpaste or mouthwash.

* * * * *